United States Patent [19]

Hunt

[11] 4,040,424
[45] Aug. 9, 1977

[54] SURGICAL PAD
[75] Inventor: James R. Hunt, Carencro, La.
[73] Assignee: Will Ross, Inc., Milwaukee, Wis.
[21] Appl. No.: 686,343
[22] Filed: May 14, 1976
[51] Int. Cl.² .............................................. A61F 13/16
[52] U.S. Cl. ................................................. 128/290 R
[58] Field of Search .............................. 128/155–157, 128/268, 287, 290 R; 206/440, 441

[56] References Cited

U.S. PATENT DOCUMENTS

| | | | |
|---|---|---|---|
| 2,353,332 | 7/1944 | Hall | 206/440 |
| 2,693,439 | 11/1954 | Blanchard et al. | 206/440 |
| 2,742,042 | 4/1956 | Flanders | 128/290 R |
| 2,742,903 | 4/1956 | Lightner | 128/290 R |
| 2,852,026 | 9/1958 | Karr | 128/290 R |
| 3,421,502 | 1/1969 | St. Clair | 128/156 |
| 3,885,566 | 5/1975 | Jacob | 128/287 |
| 3,897,783 | 8/1975 | Ginocchio | 128/290 R |

Primary Examiner—Lawrence W. Trapp
Attorney, Agent, or Firm—John A. Dhuey

[57] ABSTRACT

An absorbent surgical pad, useful after delivery, hysterectomy, or hemorrhoidectomy procedures and having a uniquely-shaped adhesive configuration, is described. There further is described a novel pad pack of such configuration that the adhesive can be removed with minimal danger of inadvertent contamination of the absorbent pad.

8 Claims, 10 Drawing Figures

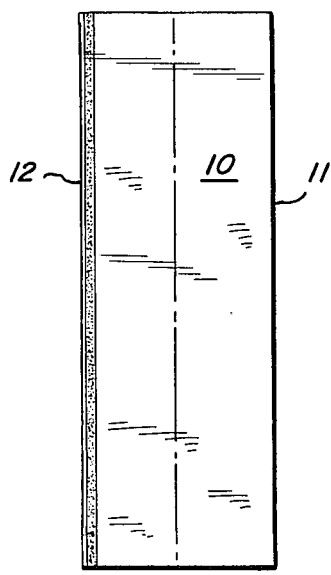
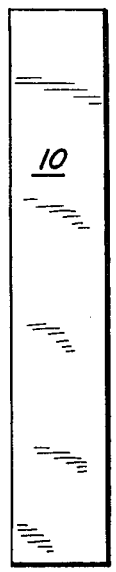
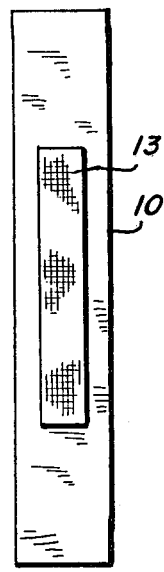
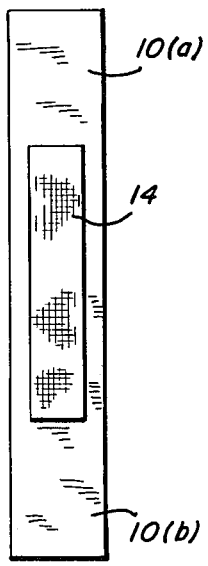
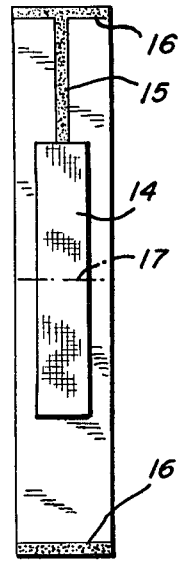
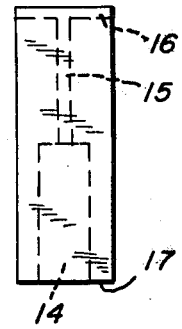
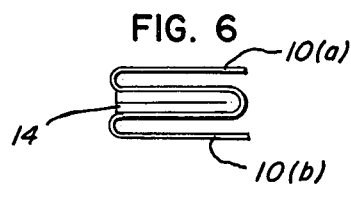
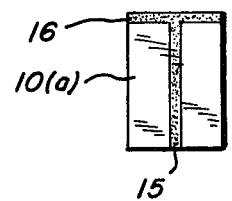

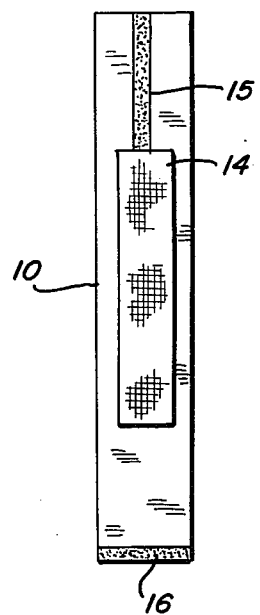
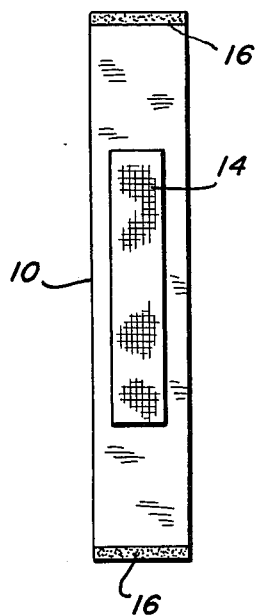

SURGICAL PAD

The present invention is concerned generally with absorbent surgical pads. More particularly it is concerned with a novel absorbent pad having a uniquely-shaped, e.g. T-shaped, adhesive configuration. Additionally, the novel configuration of the pad permits packging in a folded configuration such that the adhesive can be exposed and the pad applied to a patient with minimal danger of inadvertent contamination of the absorbent portion of the pad.

It is standard procedure after certain delivery, hysterectomy, plastic or reconstructive surgery or hemorrhoidectomy procedures to apply an absorbent pad to the affected area before the patient is removed from surgery to the hospital recovery area. Generally such pads are applied about the rectal-genital area and retained thereon by a belt passing around the patient's midsection. Such belts and pads are cumbersome to apply and are difficult to maintain at the proper position during subsequent movement of the patient.

It is thus an object of this invention to provide a disposable absorbent surgical pad which is conveniently applied and secured to a patient. It further is an object of this invention to provide an absorbent pad having pressuresensitive adhesive thereon which will retain the pad in the desired configuration and yet permit removal with a minimum discomfort to the patient. Additionally, it is an object to provide a novel, folded pad, suitable for rapid application to the patient with minimal danger of contaminating the absorbent surgical pad itself.

Those and other objects of this invention will be apparent from the following drawings in which:

FIG. 1 is a top view of one preferred embodiment of the invention;

FIG. 2 is a view of the backing sheet in its unfolded configuration;

FIG. 3 is a view of the backing sheet in its folded configuration;

FIG. 4 is a view of the backing sheet with an adhesive bead applied;

FIG. 5 is a view of the backing sheet and absorbent pad affixed thereto;

FIG. 6 is a side view of another preferred embodiment of the invention;

FIG. 7 is a top view of the pad of FIG. 6 at a stage prior to its final configuration;

FIG. 8 is a top view of the pad of FIG. 6; and FIGS. 9 and 10 are top views of alternate embodiments of the pad.

As shown in FIGS. 1-5, the pad is conveniently constructed from a backing sheet 10, formed from cloth or preferably soft, non-woven paper, having outer edges 11 and 12. A bead of adhesive is applied to outer edges 11 and 12 and the backing material is folded along a midline to present a folded configuration as shown more particularly in FIG. 3. Alternatively, backing sheet 10 may consist of a non-woven, absorbent paper having a non-absorbent plastic covering on one side thereof to prevent fluid transmission through the backing sheet. An adhesive bead then is applied as shown in FIG. 4 along the midline 13 of the folded configuration and along a substantial longitudinal portion of the pad. An absorbent pad 14 then is applied to the adhesive as shown in FIG. 5 and retained thereon. Absorbent pad 14 extends a substantial longitudinal distance on the sheet backing but not the entire length thereof to leave end portions 10a and 10b. The absorbent pad is sized for its appropriate application.

Double-backed, pressure sensitive, adhesive tape strips 15 and 16 then are applied to portions 10a and 10b as shown in FIG. 1 to provide retention means on the pad. Preferably, medical grade adhesive strips are utilized. The adhesive strips are applied in a T-shaped configuration on portion 10a of backing sheet 10. On portion 10b of backing sheet 10, strip 16 is applied horizontally along the end edgeof portion 10b. That configuration is found to be particularly advantageous in that strip 16 prevents lateral motion of such pad in application and strip 15 prevents lineal motion. As can be seen clearly in FIG. 1, strip 15 extends to absorbent pad 14. A protective covering over the adhesive strips prevents the pad from being adhered to any object until immediately before application to a patient.

The novel T-shaped adhesive configuration facilitates retention of the pad both in the lateral and lineal directions. Such retention is accomplished with the minimal use of adhesive and consequent discomfort to the patient. Portion 10a is adapted for application to the frontal area of the patient, whereas portion 10b is adapted for application to the back-side of the patient. Furthermore, the small surface area of adhesive in contact with the patient readily permits removal without further discomfort to the patient.

Another preferred embodiment of the instant pad is shown in FIG. 6 wherein the pad is arranged in a unique folded configuration with respect to adhesive strips. Pad 10 is folded inwardly upon itself along a horizontal midline 17 to provide a folded configuration as shown in FIG. 7, wherein adhesive strips 15 and 16 and absorbent 14 are within outer backing 10. Next, portions 10a and 10b are folded backwardlytoward midline 17 to overlay backing portion 10. That configuration is most clearly shown in FIG. 6 and FIG. 8 wherein portion 10a is now the top portion and portion 10b forms the bottom portion of the folded pad. Adhesive strips 15 and 16 are now exposed on the outer surfaces, whereas pad 14 is covered by backing material 10.

The configuration as shown in FIG. 6 permits handling of the completed pad with minimal danger of any contacting of absorbent portion 14. In use the folded configuration can be grasped on surfaces 10a and 10b and the protective covering on the adhesive removed without contacting pad 14. While still retaining control by handling surfaces 10a and 10b, the pad can be applied to the patient in an extended configuration and portions 10a and 10b folded downwardly to contact the patient. The now exposed adhesive strips 15 and 16 contact the skin of the patient and retain the pad in the desired configuration. It is seen readily that during the application procedure pad 14 need not in any way be contacted by the hands of the medical personnel applying the pad.

The dimensions of the pad and the particular materials of fabrication will depend to a large extent on the particular application desired. Particularly useful as backing materials are polyethylene-laminated, non-woven materials. The absorbent pad portion can be of cloth or fibrous paper, such as a conventional sanitary pad. Furthermore, convenient dimensions for most uses have been determined to be a 4-5 inch width in a completed pad and a 25-30 inch length. Absorbent pad 14 satisfactorily is 13-16 inches long and centered on backing material 10. Adhesive strips 15 and 16 are standard adhesive tape strips having adhesive on both sides of the tape. Preferred tapes are those having a covering material on each side of the tape such that one side of the covering material can be removed for application of adhesive to the pad as shown in FIG. 5. The top portions of adhesive strips 15 and 16 remain covered until immediately prior to use. As described hereinbefore the adhesive covering material is conveniently removed while the pad is in its folded configuration as shown in FIG. 6 without any danger of contacting pad 14.

The folded pad shown in FIG. 6 can be packaged in that configuration in an outer envelope impervious to microorganisms and sterilized according to conventional methods. For example, the unsterilized pad can be sealed in an outer envelope which is permeable to a sterilizing gas, such as ethylene oxide, and sterilized after packaging. Alternatively, suitable wet sterilization methods, e.g. alcohol saturation, can be used prior to packaging. Accordingly, the pad then is immediately ready for use in the above-described fashion, after removal from the protective envelope.

Alternate embodiments of the surgical pad if this invention are illustrated in FIGS. 9 and 10. Depending on the particular nature of the surgical operation and patient preparation before application of the pad, certain adhesive configurations may be preferable. Thus, in post-partum use when the patient has not been adequately prepared for delivery, e.g. in an emergency delivery situation, the pad as disclosed in FIG. 10 may be preferable since the adhesive will only contact portions of the body away from the genital area. Alternatively, after other procedures, the pad of FIG. 9 may be preferable. The single horizontal strip 16 would be applied to the back-side of the patient and the single vertical strip would be applied to the frontal area of the patient, thus minimally contacting that area of the body which may be extremely sensitive at the time of pad application.

While the invention has been illustrated particularly with respect to the embodiments described in the drawings, those figures are not meant to limit the invention in that various embodiments and modifications will be apparent to those skilled in the art without departing from the spirit and scope of this invention.

What is claimed is:

1. A surgical pad comprising a backing sheet, an absorbent pad secured to said sheet at substantially the midportion thereof, said sheet extending beyond said pad to form two end portions, and a pressure-sensitive, adhesive strip applied to one of said end portions in a T-shaped configuration, such that the horizontal portion of the T extends along the edge of said end portion and the vertical portion of the T extends between the end of said end portion and the end of said pad.

2. A pad as in claim 1, wherein said adhesive is doubly-backed, pressure-sensitive adhesive tape.

3. A surgical pad comprising an absorbent pad folded along a horizontal midline thereof, a sheet secured to the outer surfaces of said folded pad and having end portions extending beyond said pad, said end portions being folded backwardly toward the horizontal, midline fold of said pad, thereby exposing outwardly surfaces of said end portions, and pressuresensitive adhesive applied to the outwardly-facing surfaces of said end portions.

4. A pad as in claim 3, wherein the adhesive is substantially in a T-shaped configuration with the horizontal portion of the T coinciding with an end edge of the sheet.

5. A pad as in claim 4, wherein the adhesive is doubly-backed, adhesive tape.

6. A sterile surgical pad pack comprising an outer envelope impervious to microorganisms, an absorbent pad within said envelope, said pad being folded along a horizontal midline thereof and having a sheet secured to the outer surfaces thereof, said sheet having end portions extending beyond said pad, said end portions being folded backwardly toward the horizontal midline fold of said pad, thereby exposing outwardly surfaces of said end portions, and adhesive applied to the outwardly facing surfaces of said end portions.

7. A sterile pad pack as in claim 6 wherein said adhesive is substantially in a T-shaped configuration with the horizontal portion of the T coinciding with an end edge of said sheet.

8. A surgical pad comprising a backing sheet, an absorbent pad secured to said sheet at substantially the midportion thereof, said sheet extending beyond said pad to form two end portions, and a first pressure-sensitive adhesive strip extending in a T shaped configuration on one of said end portions and a second pressure-sensitive adhesive strip extending horizontally across the end edge of the other of said end portions.

* * * * *